United States Patent
Meyer et al.

(10) Patent No.: US 9,730,881 B2
(45) Date of Patent: Aug. 15, 2017

(54) COMPOSITIONS AND METHODS FOR HAIR IMPROVEMENT

(71) Applicant: Tru-Hair LLC, Carlsbad, CA (US)

(72) Inventors: Jane M. Meyer, Carlsbad, CA (US); Nikita Malavia, San Diego, CA (US); Stephen Alexander Charles, Los Altos, CA (US)

(73) Assignee: Tru-Hair LLC, Carlsbad, CA (US)

( * ) Notice: Subject to any disclaimer, the term of this patent is extended or adjusted under 35 U.S.C. 154(b) by 0 days.

(21) Appl. No.: 14/419,283

(22) PCT Filed: Jul. 24, 2013

(86) PCT No.: PCT/US2013/051769
§ 371 (c)(1),
(2) Date: Feb. 3, 2015

(87) PCT Pub. No.: WO2014/022163
PCT Pub. Date: Feb. 6, 2014

(65) Prior Publication Data
US 2015/0216780 A1    Aug. 6, 2015

Related U.S. Application Data

(60) Provisional application No. 61/679,554, filed on Aug. 3, 2012.

(51) Int. Cl.
| | | |
|---|---|---|
| *A61Q 5/12* | (2006.01) | |
| *A61K 8/65* | (2006.01) | |
| *A61K 8/73* | (2006.01) | |
| *A61Q 5/00* | (2006.01) | |
| *A61K 8/86* | (2006.01) | |
| *A45D 7/06* | (2006.01) | |

(52) U.S. Cl.
CPC ............. *A61K 8/65* (2013.01); *A45D 7/06* (2013.01); *A61K 8/73* (2013.01); *A61K 8/86* (2013.01); *A61Q 5/00* (2013.01); *A61Q 5/002* (2013.01); *A61Q 5/12* (2013.01); *A61K 2800/30* (2013.01); *A61K 2800/57* (2013.01)

(58) Field of Classification Search
None
See application file for complete search history.

(56) References Cited

U.S. PATENT DOCUMENTS

| | | | |
|---|---|---|---|
| 2,850,351 A | | 9/1958 | Moore et al. |
| 4,135,942 A | | 1/1979 | Kikkawa |
| 5,679,329 A | * | 10/1997 | Dupuis .................. A61K 8/046 424/401 |
| 8,151,624 B2 | | 4/2012 | Sherman et al. |
| 2008/0159975 A1 | | 7/2008 | Nho et al. |
| 2009/0165812 A1 | | 7/2009 | Resnick et al. |
| 2010/0132133 A1 | | 6/2010 | Zanotti Russo |
| 2012/0014887 A1 | | 1/2012 | Fournial et al. |

FOREIGN PATENT DOCUMENTS

WO    WO 2011/141882    11/2011

OTHER PUBLICATIONS

Supplementary Partial European Search Report in European Application No. EP 13820333, dated Dec. 17, 2015, 11 pages.
'ewg.org' [online]. "Brands that hide formaldehyde," Apr. 2011, [retrieved on May 26, 2015]. Retrieved from the Internet: URL <http://www.ewg.org/hair-straighteners/our-report/hair-straighteners-that-hide-formaldehyde/>. 6 pages.
International Preliminary Report on Patentability in International Application No. PCT/US2013/051769, Feb. 3, 2015, 8 pages.
International Search Report and Written Opinion in International Application No. PCT/US2013/051769, Dec. 30, 2013, 14 pages.
Slavin et al., "PEGylation of surface protein filaments: coverage and impact on denaturation," RSC Advances, Jun. 2011, 1:58-66.
Wu et al., "Determination of Formaldehyde in Cosmetics by HPLC Method and Acetylacetone Method," Journal of Food and Drug Analysis, 2003, 11(1):8-15.

\* cited by examiner

*Primary Examiner* — Jyothsna Venkat
(74) *Attorney, Agent, or Firm* — Fish & Richardson P.C.

(57) ABSTRACT

Hair improvement compositions comprising covalent conjugates of a polypeptide and a hydrophilic polymer, or a polysaccharide and a hydrophilic polymer, or both, are provided herein. Methods for improving one or more physical characteristics of hair using the described compositions are also provided. The improvements can be semi-permanent.

38 Claims, No Drawings

COMPOSITIONS AND METHODS FOR HAIR IMPROVEMENT

CROSS-REFERENCE TO RELATED APPLICATIONS

This application is a National Stage application under 35 U.S.C. §371 of International Application No. PCT/US2013/051769, filed Jul. 24, 2013, which claims the benefit of U.S. Provisional Application Ser. No. 61/679,554, filed Aug. 3, 2012. The disclosure of the prior applications are considered part of (and are incorporated by reference in) the disclosure of this application.

BACKGROUND OF THE INVENTION

1) Field of the Invention

Provided herein are compositions and methods for hair modification, and more particularly, compositions and methods that improve hair physical characteristics such as by increasing hair smoothness, strength, volume/thickness, and/or flexibility, including on a semi-permanent basis.

2) Background

There are a multitude of hair care products on the market that improve hair quality. Daily hair conditioners contain numerous ingredients that improve different aspects of hair quality including: moisturizers, reconstructors, acidifiers, detanglers, thermal protectors, glossers, oils, surfactants, lubricants, sequestrants, antistatic agents and preservatives. However, daily hair conditioners and even deep hair conditioners only provide for such improvement for a period of a few days. The benefit of most hair conditioners is lost after shampooing of the hair.

Long-term or semi-permanent hair smoothing products have been developed but have been wrought with health concerns. Several semi-permanent hair straightening products have been found to contain high levels of formaldehyde. Formaldehyde gas is released during the heating process used in the application of the product to the hair. Formaldehyde gas is a dangerous pollutant that can be severely irritating to the eyes, nose, throat, and long term exposure to formaldehyde has been associated with an increased risk of cancer. In April 2011, the U.S. Occupational Safety and Health Administration (OSHA) issued a hazard alert against the use of hair smoothing products containing formaldehyde. The Environmental Working Group investigated hair straighteners in 2011 for inclusion of formaldehyde, including formaldehyde dissolved in aqueous solutions, i.e., methylene glycol, which converts back to formaldehyde when water evaporates through the application of heat. The investigation concluded that many current products do not claim to include formaldehyde, but when tested, include significant levels of formaldehyde that exceed safety standards. See the Environmental Working Group report at www.ewg.org/hair-straighteners/our-report/hair-straighteners-that-hide-formaldehyde.

Accordingly, there is a need for compositions and methods that can be used to achieve semi-permanent smoothing, thickening and/or repair of hair that do not result in the formation of formaldehyde gas, or result in a negligible amount of formaldehyde gas formation.

SUMMARY OF THE INVENTION

The present invention answers the need for safe and effective compositions and methods used for semi-permanent hair improvement. When applied to the hair, in some cases with the application of heat, the compositions described herein provide for significant hair smoothing and thickening effects that are semi-permanent. However, unlike prior art compositions, the compositions of the present invention do not contain or release a significant amount of formaldehyde, and in some embodiments, are substantially free of formaldehyde.

Provided herein are hair improvement compositions that comprise a polypeptide covalently bound to a hydrophilic polymer and/or a polysaccharide covalently bound to a hydrophilic polymer. These compositions are preferably water soluble. In some embodiments, the hydrophilic polymer has a formula selected from:

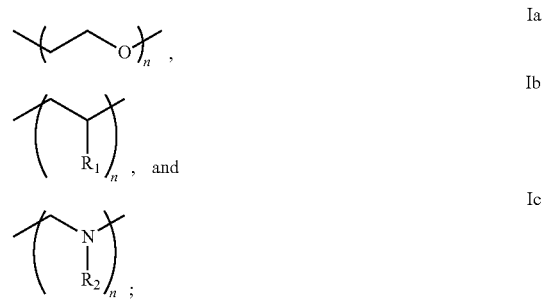

wherein $R_1$ is hydroxyl, carboxyl, ethylamine, 2-pyrrolidone, hydoxyethyl methacrylic acid, methylamine, phosphonic acid, sulfonic acid, hydroxyl, or $SO_4^-$; wherein $R_2$ is hydrogen, methyloxazoline, ethyloxazoline, or propyloxazoline; and wherein n is between 1 and 1,500.

The polypeptides bound to the hydrophilic polymer include, but are not limited to, polypeptides of keratin, collagen, elastin, fibroin, milk-derived proteins such as casein, beta-lactoglobulin and alpha-lactalbumin, and grain proteins such as wheat protein. Hydrophobic polypeptides such as keratin may be preferred in certain embodiments. Also provided herein are compositions comprising a hydrophilic polymer covalently bound to a polysaccharide such as chitosan, chitin, or chitin glucan.

It is a surprising finding of the present invention that compositions comprising a hydrophilic polymer covalently bound to a keratin polypeptide provide semi-permanent hair improvement effects. Tables 1-4 below demonstrate that a polyethylene glycol polymer covalently attached to a keratin polypeptide can be applied to hair along with heat to achieve an increase in hair thickness (Column 1), and an increase in hair smoothness (Columns 2 & 3). Table 4 further demonstrates that a keratin polypeptide-polymer conjugate has a greater improvement effect than either keratin polypeptide alone or hydrophilic polymer alone. These effects remain for up to 135 washes, making the effects semi-permanent. (See Table 2.)

DETAILED DESCRIPTION OF THE INVENTION

1) Initial Definitions

As used in the specification and the claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from any isolation or purification method and would not exclude pharmaceutically acceptable carriers, such as preservatives, phosphate buffered saline and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

An "effective amount" is an amount sufficient to effect beneficial or desired results. An effective amount can be administered in one or more administrations, applications or dosages.

A "pharmaceutical composition" is intended to include the combination a composition as described herein, with a carrier, whether inert or active, making the composition suitable for diagnostic, cosmetic, dermatological, or therapeutic use in vitro, in vivo, or ex vivo.

As used herein, the term "pharmaceutically acceptable carrier" encompasses any of the standard pharmaceutical carriers, and can include components such as, without limitation, water, buffers (e.g., phosphate buffered saline or saline), pH modifiers, stabilizers, preservatives, bactericides, skin conditioners, fixatives and emulsions, such as an oil/water emulsion and various types of wetting agents. In some embodiments, the carriers include stabilizers, buffers, pH modifiers, and preservatives suitable for inclusion in hair care, dermatological, or cosmetic applications.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA (tRNA), ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides may be interrupted by non-nucleotide components. A polynucleotide can be further modified after polymerization, such as by conjugation with a labeling component. The term "polynucleotide" also refers to both double- and single-stranded molecules. Unless otherwise specified or required, any embodiment of this invention that is a polynucleotide encompasses both the double-stranded form and each of the two complementary single-stranded forms known or predicted to make up the double-stranded form.

The terms "subject," "individual," and "patient" are used interchangeably herein and refer to a vertebrate, preferably a mammal, more preferably a human. Mammals include, but are not limited to, primates (e.g., humans), cows, sheep, goats, horses, dogs, cats, rabbits, rats, mice and the like.

2) Description and Further Definitions

Provided herein are compositions and methods for improving hair by increasing one or more of its physical characteristics, including its smoothness, strength, volume/thickness, and/or flexibility. In some cases, the methods result in the improvement of one or more physical characteristics on a semi-permanent basis. The hair improvement compositions comprise a polypeptide covalently bound to a hydrophilic polymer and/or a polysaccharide covalently bound (conjugated) to a hydrophilic polymer. In some embodiments, the compositions can further include one or more of unconjugated hydrophilic polymer, unconjugated polypeptide, and unconjugated polysaccharide. In some embodiments, the compositions are substantially free of formaldehyde. In some embodiments, the methods do not result in the release of substantial amounts of formaldehyde. The methods comprise applying the hair improvement compositions to at least a portion of a subject's hair and applying heat to the hair. In some embodiments, the hair is allowed to air dry prior to application of the heat. Heat can be applied through any method, such as by drying the hair with a hair dryer or the use of a flat iron, and can include the use of one or more heating methods, such as by both drying the hair with a hair dryer and using a flat iron. Such methods can result in a semi-permanent increase in hair smoothness, hair thickness, hair strength and/or hair flexibility.

As used herein, the term "hydrophilic polymer" includes polypeptides, carbohydrates, nucleic acids, poly(ethylene glycol), poly(oxazoline), poly(vinylpyrrolidone), poly(acrylamide), poly(acrylic acid), poly(allylamine), poly(hydroxyethyl methacrylate), poly(ethyleneimine), poly(vinylphosphonic acid), poly(vinyl sulfate), poly(vinylsulfonic acid), poly(vinyl alcohol), glycerol propoxylate, hydroxyethyl starch (HES). In one embodiment, the hydrophilic polymer is a synthetic hydrophilic polymer selected from the group consisting of: poly(ethylene glycol), poly(oxazoline), poly(vinylpyrrolidone), poly(acrylamide), poly(acrylic acid), poly(allylamine), poly(hydroxyethyl methacrylate), poly(ethyleneimine), poly(vinylphosphonic acid), poly(vinyl sulfate), poly(vinylsulfonic acid), poly(vinyl alcohol), glycerol propoxylate, and hydroxyethyl starch (HES). In some embodiments, the molecular weight of the hydrophilic polymer is between about 0.5 and about 80 kDa, between about 0.5 and about 40 kDa, or between about 0.5 and about 10 kDa. In some embodiments, the molecular weight is between about 2 and about 10 kDa. In some embodiments, the molecular weight is between about 20 and about 40 kDA. In one embodiment, the molecular weight of the hydrophilic polymer is about 5 kDa. In another embodiment, the molecular weight of the hydrophilic polymer is about 30 kDa.

In other or further embodiments, the hydrophilic polymer has a formula selected from:

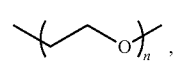
Ia

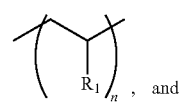
, and
Ib

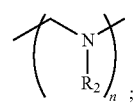
;
Ic wherein R1 is hydroxyl, carboxyl, ethylamine, 2-pyrrolidone, hydoxyethyl methacrylic acid, methylamine, phosphonic acid, sulfonic acid, hydroxyl, or $SO_4^-$; wherein $R_2$ is hydrogen, methyloxazoline, ethyloxazoline, or propyloxazoline; and wherein n is between 1 and 1,500. In some embodiments, the "n" in formula Ia, Ib or Ic is between 1 and 1000, 1 and 500, 1 and 250, or 1 and 125. In a preferred embodiment, the "n" in formula Ia, Ib or Ic is between 100 and 125, and more preferably 114. In still other embodiments, the "n" in formula Ia, Ib or Ic may be selected from 1, 2, 3, 4, 5, 6, 7, 8, 9, 10, 11, 12, 13, 14, 15, 16, 17, 18, 19, 20, 21, 22, 23 or 24.

Provided herein are compositions that include a hydrophilic polymer covalently bound (or conjugated) to a polypeptide. The term "covalently bound" means that a covalent bond exists between a portion of the hydrophilic polymer and the polypeptide, or vice-versa. Accordingly, covalently bound refers to both direct covalent bonds (a sharing of pairs of electrons between the atoms of the hydrophilic polymer and the polypeptide) and indirect covalent bonds (a sharing of pairs of electrons between atoms of the hydrophilic polymer and the composition comprising the polypeptide, or vice-versa). The covalently bound polymer and polypeptide (or covalently bound polymer and polysaccharide) can be referred to as a conjugate or covalent conjugate herein.

As used herein, the term "polypeptide" is used in its broadest sense to refer to a compound of two of more subunit amino acids, amino acid analogs, or peptidomimetics. The subunits may be linked by peptide bonds. In another embodiment, the subunits may be linked by other bonds, e.g., ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids may be referred to as an oliogpeptide if the peptide chain is short, e.g., less than about 25 amino acids. The term "polypeptide" can include full-length naturally occurring proteins as well as functional fragments of those proteins. Protein fragments are functional when they achieve the desired result of the full-length protein in the context of the present invention. For example, a keratin fragment that is covalently bound to a hydrophilic polymer is encompassed by the present invention when the keratin-hydrophilic polymer provides a hair improvement effect when applied to hair using the methods of the present invention. A polypeptide can be derived from natural sources or synthetically prepared, including through the use of large-scale protein expression mechanisms.

It should also be understood that the polypeptide constituent of the polypeptide-hydrophilic polymer composition can be any polypeptide that provides a hair improvement effect when applied to hair according to the present invention. These polypeptides include, but are not limited to, polypeptides of keratin, collagen, elastin, fibroin, milk-derived proteins such as casein, beta-lactoglobulin and alpha-lactalbumin, and grain proteins such as soy protein, corn protein and wheat protein. Hydrophobic polypeptides such as keratin may be preferred in certain embodiments. The polypeptides may be hydrolyzed or non-hydrolyzed, and in some embodiments, the polypeptides are non-hydrolyzed.

In some embodiments, the hydrophilic polymer is covalently bound to one or more of a keratin polypeptide, a collagen polypeptide, an elastin polypeptide, a fibroin polypeptide, a chitin polysaccharide or a chitosan polysaccharide. In other embodiments, the hydrophilic polymer is covalently bound to a keratin polypeptide, a collagen polypeptide, an elastin polypeptide, or a fibroin polypeptide. In still other embodiments, the hydrophilic polymer is covalently bound to a keratin polypeptide.

The term "keratin" refers to a family of fibrous structural proteins that are found in the hair, skin, nails, claws and hooves of mammals (α-keratins) and in the scales, claws and shells of reptiles, the feathers, beaks, and claws of birds and the quills of porcupines (β-keratins). Alpha-keratins are also known as cytokeratins and are further subdivided into soft α-keratins (epithelial cytokeratins) and hard α-keratins (trichocyte keratins). All keratins are heteropolymers of type I and type II keratins. The HUGO Gene Nomenclature Committee identifies the following as known keratin polypeptide encoding genes: KRT1, KRT2, KRT3, KRT4, KRT5, KRT6A, KRT6B, KRT6C, KRT7, KRT8, KRT9, KRT10, KRT12, KRT13, KRT14, KRT15, KRT16, KRT17, KRT18, KRT19, KRT20, KRT23, KRT24, KRT25, KRT26, KRT27, KRT28, KRT31, KRT32, KRT33A, KRT33B, KRT34, KRT35, KRT36, KRT37, KRT38, KRT39, KRT40, KRT71, KRT72, KRT73, KRT74, KRT75, KRT76, KRT77, KRT78, KRT79, KRT80, KRT81, KRT82, KRT83, KRT84, KRT85, KRT86, KRT222. Accordingly, a keratin polypeptide of the present invention may be encoded by one or more genes selected from KRT1, KRT2, KRT3, KRT4, KRT5, KRT6A, KRT6B, KRT6C, KRT7, KRT8, KRT9, KRT10, KRT12, KRT13, KRT14, KRT15, KRT16, KRT17, KRT18, KRT19, KRT20, KRT23, KRT24, KRT25, KRT26, KRT27, KRT28, KRT31, KRT32, KRT33A, KRT33B, KRT34, KRT35, KRT36, KRT37, KRT38, KRT39, KRT40, KRT71, KRT72, KRT73, KRT74, KRT75, KRT76, KRT77, KRT78, KRT79, KRT80, KRT81, KRT82, KRT83, KRT84, KRT85, KRT86, and KRT222.

In one embodiment, the hydrophilic polymer is covalently bound to a keratin polypeptide and the hydrophilic polymer is selected from the group consisting of: poly(ethylene glycol), poly(oxazoline), poly(vinylpyrrolidone), poly(acrylamide), poly(acrylic acid), poly(allylamine), poly(hydroxyethyl methacrylate), poly(ethyleneimine), poly(vinylphosphonic acid), poly(vinyl sulfate), poly(vinylsulfonic acid), poly(vinyl alcohol), glycerol propoxylate, and hydroxyethyl starch (HES). The keratin polypeptide can be naturally derived or synthetically prepared. The keratin polypeptide can be purified from various natural sources or commercially obtained. The keratin polypeptide can have a molecular weight from about 0.5 kDa to about 60 kDa, or from about 2 kDa to about 6 kDA, or from about 20 kDa to about 40 kDa. In some embodiments, the keratin polypeptide is about 5 kDa. In some embodiments, the keratin polypeptide is about 45 to about 55 kDa.

In some embodiments, the hydrophilic polymer is covalently bound to a keratin polypeptide and the hydrophilic polymer has a formula selected from:

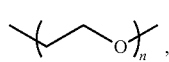

Ia

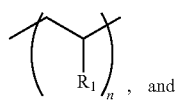

, and

Ib

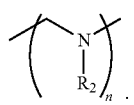

.

Ic wherein R1 is hydroxyl, carboxyl, ethylamine, 2-pyrrolidone, hydoxyethyl methacrylic acid, methylamine, phosphonic acid, sulfonic acid, hydroxyl, or $SO_4^-$; wherein $R_2$ is hydrogen, methyloxazoline, ethyloxazoline, or propyloxazoline; and wherein n is between 1 and 1,500. In some embodiments, the "n" in formula Ia, Ib or Ic is between 1 and 1000, 1 and 500, 1 and 250, or 1 and 125. In a preferred embodiment, the "n" in formula Ia, Ib or Ic is between 100 and 125, and in some embodiments, is about 114. In still other embodiments, the "n" in formula Ia, Ib or Ic may be selected from 1, 2, 3, 4, 5, 6, 7, 8, 9, 10, 11, 12, 13, 14, 15, 16, 17, 18, 19, 20, 21, 22, 23 or 24.

In yet another embodiment, the hydrophilic polymer is covalently bound to a keratin polypeptide and the hydrophilic polymer has a formula of:

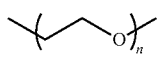

Ia wherein n is between 1 and 1500. In some embodiments, the "n" in formula Ia, Ib or Ic is between 1 and 1000, 1 and 500, 1 and 250, or 1 and 125. In a preferred embodiment, the "n" in formula Ia, Ib or Ic is between 100 and 125, and more preferably about 114. In still other embodiments, the "n" in formula Ia, Ib or Ic may be selected from 1, 2, 3, 4, 5, 6, 7, 8, 9, 10, 11, 12, 13, 14, 15, 16, 17, 18, 19, 20, 21, 22, 23 or 24.

Also provided herein are compositions comprising a hydrophilic polymer covalently bound to a polysaccharide such as chitosan, chitin or chitin glucan. When the hydrophilic polymer is bound to a polysaccharide, the polysaccharide may be oxidized to yield aldehydes on the sugar residues, which aldehydes are then conjugated to hydroxylamine or oxime functional hydrophilic polymers.

The compounds of formula Ia are known to those of skill in the art as polyethylene glycol, or PEG, compounds. There are a wide range of PEG compounds that may be used in the present invention—these compounds may be linear or branched, reactive on one or both ends (mono- or bi-functional), or non-reactive in the traditional sense. The PEG compounds encompassed by the present invention are capable of being covalently bound to a polypeptide or a polysaccharide at reactive moiety on the polypeptide or polysaccharide, or a polypeptide or polysaccharide modified to include such a reactive moiety, however, the invention is not limited by the covalent attachment method. In some embodiments, the PEG compound is functionalized to allow reaction with the polypeptide or polysaccharide. In some embodiments, the hydrophilic polymer is a PEG compound that covalently binds a polypeptide at a primary amine (e.g. a lysine residue). In other embodiments, the hydrophilic polymer is a PEG compound that covalently binds a polypeptide at a sulfhydryl (e.g. a cysteine residue).

Non-limiting examples of hydrophilic PEG polymers that fall within the present invention include functionalized PEGs having the trade names MS(PEG)$_4$ (Thermo Scientific, Rockford, Ill., USA), MS(PEG)$_8$ (Thermo Scientific, Rockford, Ill., USA), MS(PEG)$_{12}$ (Thermo Scientific, Rockford, Ill., USA), MS(PEG)$_{24}$ (Thermo Scientific, Rockford, Ill., USA), TMS(PEG)$_{12}$ (Thermo Scientific, Rockford, Ill., USA), TMM(PEG)$_{12}$ (Thermo Scientific, Rockford, Ill., USA), MM(PEG)12 (Thermo Scientific, Rockford, Ill., USA), MM(PEG)$_{24}$ (Thermo Scientific, Rockford, Ill., USA), and other N-hydroxysuccinimide functionalized PEGs, mPEG-Succinimidyl-Succinate (molecular weight of 2, 5, 10, 20 or 30 kDa) (Laysan Bio., Inc., Arab, Ala., USA), mPEG-Nitrophenyl carbonate (molecular weight of 2, 5, 10, 20, or 30 kDa) (Laysan Bio., Inc., Arab, Ala., USA), and mPEG-Succinimidyl Glutarate (molecular weight of 2, 5, 10, 20 or 30 kDa) (Laysan Bio., Inc., Arab, Ala., USA). "Branched" polyethylene glycol compositions include TMS (PEG)$_{12}$, TMM(PEG)$_{12}$, and any other multi-armed polyethylene glycol compositions. In one embodiment, the hydrophilic polymer is an mPEG-Succinimidyl-Succinate polymer that is about 5 kDa and wherein "n" is about 114.

It is a surprising finding of the present invention that compositions comprising a hydrophilic polymer covalently bound to a keratin polypeptide provide semi-permanent hair improvement effects. Tables 1-4 below demonstrate that a polyethylene glycol polymer covalently attached to a keratin polypeptide can be applied to hair along with heat to achieve an increase in hair thickness (Column 1), and an increase in hair smoothness (Columns 2 & 3). Table 4 further demonstrates that a keratin polypeptide-polymer combination has a greater improvement effect than either keratin polypeptide alone or hydrophilic polymer alone. These effects remain for up to 135 washes, making the effects semi-permanent. (See Table 2.)

The term "semi-permanent" is defined herein to mean an effect existing beyond 10 hair washings or existing longer than one week following application of a hair improvement composition to the hair. In some embodiments, a semi-permanent effect exists after 25, 50, 100, or 200 hair washings following the application of the hair improvement composition to the hair. In other or further embodiments, a semi-permanent effect exists after 7, 14, 30, 60, 90, 120 or 180 days after the application of the hair improvement composition to the hair. Table 3 demonstrates that semi-permanent hair improvement effects of the present invention can be achieved in multiple different types of hair, including African American hair.

Accordingly, provided herein is a method of improving one or more physical characteristics of hair comprising contacting a least a portion of a subject's hair with a composition comprising a hydrophilic polymer-polypeptide conjugate or a hydrophilic polymer-polysaccharide conjugate, or both, and applying heat to the contacted hair. In some embodiments, the method includes allowing the hair to air dry before application of the heat. Heat can be applied by any mechanism, such as by drying the hair via the use of a hair dryer or through the use of a flat iron, or in some embodiments, both.

It should be understood that the hair improvement composition can contain a mixture of covalently bound hydrophilic polymer and polypeptide, covalently bound hydrophilic polymer and polysaccharide, free hydrophilic polymer, free polypeptide, and/or free polysaccharide (wherein "free" means not covalently bound). In some embodiments, a hydrophilic polymer is chosen that has a polypeptide or polysaccharide reaction time greater than 15 minutes, greater than 20 minutes, or greater than 30 minutes, in order to increase the amount of free hydrophilic polymer, hydrophilic polypeptide, and/or hydrophilic polysaccharide in the hair improvement composition. In other embodiments, a hydrophilic polymer is chosen that has a reaction time of less than 15 minutes, less than 10 minutes, or less than 5 minutes in order to increase the amount of the covalent conjugate in the hair improvement composition. In some embodiments, the ratio of the polypeptide or the polysaccharide to the hydrophilic polymer during the conjugation reaction can range from about 5:0.1 to about 0.1:5. In some embodiments, the ratio is about 1:1. In some embodiments, the ratio is about 1:0.3. In some embodiments, the ratio is about 1:0.1.

In some embodiments, the hair improvement compositions can include pharmaceutically acceptable carriers as described previously. In some embodiments, the hair improvement compositions include one or more buffer components. In some embodiments, the hair improvement compositions include one or more preservatives. Suitable examples include, without limitation, phenoxyethanol, citric acid, potassium sorbate, and caprylyl glycol.

The methods provided herein may be used to achieve multiple hair improvement effects. As used herein, the term "hair improvement effect" includes, but is not limited to, smoothing, thickening, repair, increased flexibility, and coating. Hair smoothing may be measured using any method known to one of skill in the art, including but not limited to, scanning electron microscopy (SEM) of the hair shaft, and the methods described in U.S. Pat. No. 8,151,624. When using SEM, hair smoothing may be indicated by an increase in either the number of tight junctions between the hair cuticle plates or a decrease in the degree of openness in the junctions between the hair cuticle plates. Hair thickening is defined herein as an increase in hair shaft diameter by greater than 15 microns. In some embodiments, hair thickening is an increase in hair shaft diameter by 16-80 microns, 20-70 microns, 25-50 microns, or 30-40 microns. Increased flexibility of the hair may be measured by a decrease in hair breakage, by an increase in tensile strength, or any other method known to those of skill in the art. Methods of measuring tensile strength are known to those of skill in the art and can take into account Hooke's Law, Young's modulus (or the module of elasticity), yield strength, alternate moduli, and strain.

The hair improvement compositions of the present invention are preferably applied directly to the hair as a topical formulation. While it is possible for the composition of the present invention to be administered alone, it is preferable to present it as a pharmaceutical formulation comprising at least one conjugate as described herein (i.e., a polypeptide or polysaccharide covalently bound to a hydrophilic polymer) together with one or more pharmaceutically acceptable carriers therefor and optionally other cosmetic or therapeutic agents. Each carrier and agent must be "acceptable" in the sense of being compatible with the other ingredients of the formulation and not injurious to the subject to which it is administered.

According to the present invention, hair improvement compositions and pharmaceutical carriers that contain or release high amounts of formaldehyde are not considered to be pharmaceutically acceptable compositions or carriers. "High" amounts of formaldehyde are amounts in excess of 10%, 5%, 2%, 1%, or 0.1%. In some embodiments, a composition described herein is substantially free of formaldehyde. As used herein, "substantially free of formaldehyde" means a non-detectable reading using the JP colorimetric assay as described further herein, or a reading less than 10 ppm using an HPLC assay for formaldehyde as described further herein. In some embodiments, a composition described herein results in a less than 8 ppm, a less than 6 ppm, or a less than 5 ppm formaldehyde result when tested using the HPLC assay.

In some embodiments, the hair improvement composition comprises a pharmaceutically acceptable carrier such as water, phosphate buffered saline, saline, and one or more additives selected from citric acid, phenoxyethanol, potassium sorbate, and citric acid. In a preferred embodiment, the pharmaceutically acceptable carrier comprises a water-based solvent and the hair improvement composition is soluble therein. It should also be understood that the present invention encompasses hair improvement compositions that are water soluble and thus capable of being mixed with water for subsequent application to hair.

Pharmaceutical compositions for topical administration according to the present invention may be formulated as an ointment, cream, suspension, lotion, powder, solution, paste, gel, spray, aerosol or oil. These pharmaceutical compositions may also contain one or more excipients or diluents. Thickening agents, emollients, and stabilizers can be used to prepare the topical compositions of the present invention. Examples of thickening agents include petrolatum, beeswax, xantham gum, or polyethylene glycol, humectants such as sorbitol, emollients such as mineral oil, lanolin and its derivatives, or squalene.

According to the methods of the present invention, the hair improvement composition is contacted with at least a portion of a subject's hair and heat is applied to the hair. IN some embodiments, the hair is allowed to air dry before application of heat. The hair improvement compositions can remain on the hair before applying heat, such as through drying the hair or through a flat iron, for any amount time including, but not limited to, one second to two hours. While the Examples below provide instances wherein the hair is dried with a hair dryer following application, it is to be understood that the hair can also dry naturally or by any other method. Heat can be applied to the hair via any mechanism including, but not limited to, flat iron, curling iron, blow dryers, and heated metal brushes. Heat can be applied via any one of these mechanisms once or multiple times. In one embodiment, heat is applied to the hair using a flat iron. In a further embodiment, heat is applied to the hair using a flat iron moved along the hair at a rate of about 5 mm/second to 20 mm/second. The flat iron may be moved along the hair at a rate of about 5, 6, 7, 8, 9, 10, 11, 12, 13, 14, or 15 mm/second. The heat applied to the hair following application of the hair improvement composition can range between 35° C. and 500° C. In some embodiments, the heat is between 50° C. and 400° C., between 100° C. and 300° C., between 150° C. and 250° C., or between 200° C. and 250° C.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All publications, patents and patent applications cited herein are hereby incorporated by reference in their entirety for all purposes.

EXAMPLES

Example 1

Preparation of Keratin-polyethylene Glycol Compositions

Keratin-polyethylene glycol compositions were prepared using the following equipment and materials:

1. Vortexer
2. Shaker
3. Pipettes (1000 μl)
4. Syringes (1 cc)
5. 1.50 ml tubes
6. Weighing balance Mettler Malani Ser#172447
7. Fume hood
1. DPBA—Dulbecco's phosphate buffered saline (1×) Cat# 14190-144, lot # 901681, Gibco Invitrogen.
2. N,N-dimethyl formamide, Cat # D119-500, lot #963760
3. MS(PEG)$_4$; [MS4] Cat#22341, lot # MI162217, Thermo Scientific (Pierce)
4. MS (PEG)$_{12}$; [MS12] Cat#22685, lot#MI162218, Thermo Scientific (Pierce)
5. MS (PEG)$_{24}$; [MS24] Cat#22687, lot#MH161869, Thermo Scientific (Pierce)
6. TMS (PEG)$_{12}$; [TMS12] Cat#22421, lot#MD157106, Thermo Scientific (Pierce)
7. Keratin [K] Cat# K3030, lot#1AG0185, Spectrum Using the above described materials and equipment, 10 mg of Keratin powder was placed in 1.5 ml centrifuge tubes (5 in number). The five samples were labeled K, K+MS4, K+MS12, K+MS24, and K+TMS12. One ml of phosphate buffered saline (PBS) was added to each of the 10 mg keratin samples and let shake for 45 minutes. Then 15 μl of about 250 mM MS4, MS12, MS24 and TMS12 pegylation stock solutions were added to each keratin sample tube and placed on a shaker for 30 minutes. The pegylation stock solutions were prepared using the following calculations:

Keratin M.W.=52.5 kDa 1 ml Conjugated protein×10 mg/1 mL×1/52500×20/1=0.003809 mmol pegylated reagent. Then 0.003809×1,000,000 μL/L×L/250 mmol=15.23.

About 15 μL of 250 mM pegylation reagent stock. Materials were equilibrated at room temperature.
a. MS4 1.1 ml DMF to 100 mg of stock MS4
b. MS12 485 μl DMF to 100 mg of stock MS12
c. MS24 230 μl DMF to 100 mg of stock MS24
d. TMS12 65 μl DMF to 100 mg of stock TMS12

The resultant solutions were stored in a freezer box with desiccant and returned to −20° C. freezer until used.

Example 2

Treatment of Human Hair with Keratin-polyethylene Glycol Compositions

Human hair samples were treated with pegylated solutions and one sample of keratin listed as prepared according to Example 1 for between one and five minutes. Control samples of untreated (standard) hair and no heat application (room temperature) were also analyzed. In addition, commercially available product, Brazilian Blowout Original Solution™, was used as a comparison, which based on its packaging includes the following ingredients:

Brazilian Blowout Original™ Solution: Water, methylene glycol, beheenyl trimethylammonium, metholsulfate and N-hexadeconol and butylene glycol mixture, isoparaffin, cetrimonium chloride, petroletum, hypnea musciformis extract (and) *Gelidiela acerosa* extract (and) *sargassum filipendula* extract (and) Sorbitol, *theobrama grandiflorum* seed butter (cupuacu butter), panthenol, hydrolyzed keratin, fragrance, methylchloroisothiazolinone, methylisothiazolinone.

All hair samples were blown dry with a hair dryer and then treated with a flat iron with one pass over the hair. The flat iron was at setting (30) which indicated a temperature of about 446° F./230° C. and was passed over the hair at a rate of about 10 mm/second. All hair samples were rinsed with tap water for about 30 seconds.

The hair samples were then treated with hair masque/mask and allowed to set for 5 minutes. The hair samples were rinsed with tap water for 30 seconds to 1 minute until all of the hair masque material was removed and then dried using a hair dryer until fully dried. Each hair sample was analyzed for hair thickening and hair smoothing as determined by scanning electron microscopy (SEM). Hair samples were also analyzed visually without the aid of a microscope. Table 1 below provides the results of these experiments. In Table 1, T=tight, L=loose, ML=medium loose, S=smooth, R=rough, and MR=medium rough.

TABLE 1

| Sample | Results (microns) | Tight plates | Smooth surface | Observations |
|---|---|---|---|---|
| Standard Hair | 50 | L | R | Light looking and dull |
| Brazilian Blowout Original Solution | 70 | L | R | Light looking and hazy |
| Keratin + MS4 | 90 | ML | MR | Smooth with color |
| Keratin + MS24 | 90 | T | S | Smooth with color |
| Keratin + TMS12 | 80 | T | S | Noticeable signs of smoothing |
| Keratin | 70 | T | S | Light looking and hazy |
| Standard hair treated Keratin: MS-12 (room temperature application) | 80 | L | R | Very loose and rough with poor properties for hair |

Table 1 shows that treatment of the hair with a keratin polypeptide covalently bound to a polyethylene glycol polymer resulted in increased hair shaft diameter (hair thickening) and tightening of the hair shaft plates (hair smoothing), and an increase in hair shaft smoothness (hair smoothing). These increases were found to be greater than those obtained with commercially available Brazilian Blowout Original Solution™.

Example 3

Treatment of Caucasian Hair with Keratin-polyethylene Glycol Compositions and Analysis of the Longevity of the Hair Improvement Effects Untreated blond Caucasian hair was prepared and treated with the MS12+K pegylation solution described in Example 1. Once the solution was applied to all of the hair, the hair was blown dry with a hair dryer and then treated with a flat iron with one pass over the hair. The flat iron was at setting (30) which indicated a temperature of about 446° F./230° C. and was passed over the hair at a rate of about 10 mm/second. The hair was rinsed with tap water for about 30 seconds. The hair was then treated with hair masque/mask and allowed to set for 5 minutes. The hair was rinsed with tap water for 30 seconds to 1 minute until all of the hair masque material was removed and then dried using a hair dryer until fully dry.

The hair was then washed with a simple and gentle shampoo (Johnson & Johnson baby shampoo, original formula). The hair was washed a sequence of times from 1 wash to 135 washes. Samples of the hair were obtained on every 5th wash 1, 5, 10, 15, up to 135. Each hair sample was then analyzed for hair thickening and hair smoothing as determined by scanning electron microscopy (SEM). Hair samples were also analyzed visually without the aid of a microscope. Table 2 below provides the results of these analyses. In Table 2, T=tight, L=loose, ML=medium loose, S=smooth, R=rough, and MR=medium rough.

TABLE 2

| Sample | Results (microns) | Tight plates | Smooth surface | Observations |
| --- | --- | --- | --- | --- |
| Standard hair treated Keratin: MS-12 (30 washes) | 90 | T | MR | Hair remained smooth, straight and had color |
| Standard hair treated Keratin: MS-12 (65 washes) | 70 | R | MR | Hair remained smooth, straight and had color |
| Standard hair treated Keratin: MS-12 (100 washes) | 85 | T | MR | Hair remained smooth, straight and had color |
| Standard hair treated Keratin: MS-12 (135 washes) | 80 | T | MR | Hair remained smooth, straight and had color |

Table 2 demonstrates that the hair improvement effects of the keratin-polyethylene glycol compositions are semi-permanent. Even after 135 washings of the hair, the hair maintained the thickening smoothing effects seen immediately after treatment of the hair.

Example 4

Treatment of African American Human Hair with Keratin-polyethylene Glycol Compositions and Analysis of the Longevity of the Hair Improvement Effects Untreated African American virgin hair (uncolored or otherwise processed) was prepared and treated with the MS12+K pegylation solution described in Example 1. Once the solution was applied to all of the hair, the hair was blown dry with a hair dryer and then treated with a flat iron with one pass over the hair. The flat iron was at setting (30) which indicated a temperature of about 446° F./230° C. and was passed over the hair at a rate of about 10 mm/second. The hair was rinsed with tap water for about 30 seconds. The hair was then treated with hair masque/mask and allowed to set for 5 minutes. The hair was rinsed with tap water for 30 seconds to 1 minute until all of the hair masque material was removed and then dried using a hair dryer until fully dried. Hair samples were obtained and analyzed for hair thickening and hair smoothing as determined by scanning electron microscopy (SEM). Hair samples were also analyzed visually without the aid of a microscope. Table 3 below provides the results of these experiments. In Table 3, T=tight, L=loose, ML=medium loose, S=smooth, R=rough, and MR=medium rough.

TABLE 3

| Sample | Results (microns) | Tight plates | Smooth surface | Observations |
| --- | --- | --- | --- | --- |
| African American Hair Standard | 60 | L | R | Highly curly |
| African American Hair treated | 60 | T | S | Tight hold on the plates, and hair was |

TABLE 3-continued

| Sample | Results (microns) | Tight plates | Smooth surface | Observations |
| --- | --- | --- | --- | --- |
| Keratin: MS-12 (135 washes) | | | | still straight after treatment and had shine |

Table 3 demonstrates that the keratin-polyethylene glycol compositions of the present invention not only provide for smoothing and thickening of Caucasian hair, but these compositions also provide smoothing and thickening effects to African American hair. These smoothing and thickening effects are further demonstrated to be semi-permanent since the hair still retained the hair improvement effect after 135 washes.

Example 5

Preparation of Keratin-polyethylene Glycol (SVA) Compositions

Keratin-polyethylene glycol compositions were prepared using the following materials and equipment:
1. Pipettes
2. Syringes
3. 1.5 ml centrifuge tubes
4. Weighing balance Mettler
5. Methoxy-Poly (Ethylene Glycol)-Succinimidyl Valerate lot# 120-176; Laysan Bio Inc. 5000 MW (SVA PEG) (5 k SVA PEG)
6. DPBS-Dulbecco's phosphate buffered saline cat# 14190, lot# 1048427, Gibco
7. Keratin Cat#K3030, lot#1AG0185, Spectrum Using the above-described materials and equipment, reaction samples were prepared having different ratios of keratin polypeptide and SVA PEG polymer (1:1, 1:0.3, 1:0.1). Samples were also prepared that contained only SVA PEG polymer as prepared according to this example (SVA Neat), only TMS-12 polymer as prepared according to Example 1 (TMS-12 Neat), only MS-24 polymer as prepared according to Example 1 (MS-24 Neat), and only PBS (Solution Neat). These samples were prepared as follows:

In 1.5 ml centrifuge tubes 1 ml of DPBS was added. Sample tubes were labeled as follows:
1. SVA Neat=weighted out 10 mg of SVA PEG and added to 1 ml D-PBS.
2. K:P; 1:1=weighted out 50 mg of SVA PEG and added to 1 ml D-PBS+5 mg keratin
3. K:P; 1:0.1=weighted out 10 mg of SVA PEG and added to 1 ml D-PBS+10 mg Keratin
4. K:P; 1:0.3=weighted out 30 mg of SVA PEG and added to 1 ml D-PBS+10 mg Keratin
5. PBS neat=1 ml of D-PBS
6. TMS12 neat=65 µl of TMS-12 added to 1 ml D-PBS
7. MS24 neat=230 µl of MS24 added to 1 ml D-PBS Different amounts [0, 5, 10 mg] of keratin were then added to 1 ml D-PBS from and shaken by hand to solubilize. Varying amount of SVA PEG were weighted out and added to the PBS-keratin solutions. The SVA PEG amounts ranged from 10 to 50 mg. Tubes were then shaken by hand and sealed with parafilm.

For the MS24 neat sample, 230 µl of stock prepared according to Example 1 was added to 1 ml D-PBS. For the TMS12 neat sample 65 µl of stock prepared according to Example 1 was added to 1 mL D-PBS.

Example 6

Preparation of Polypeptide-polyethylene Glycol and Polysaccharide-polyethylene Glycol Compositions Protein-polyethylene glycol and polysaccharide-polyethylene glycol compositions were prepared using the following equipment and materials:
1. Vortexer
2. Shaker
3. Pipettes (1000 µl)
4. Syringes (1 cc)
5. 1.50 ml tubes
6. Weighing balance Gemini-20 AWS
1. DPBA—Dulbecco's phosphate buffered saline (1×) Cat# 14190-144, lot # 901681, Gibco Invitrogen.
2. mPEG-SVA [SVA] Lot#130-143, Laysan Bio
3. mPEG-NPC [NPC]Cat#PINPC-5, Lot#CINPC-005-12066
4. Collagen Cat#C2477, lot#WL0663, Spectrum
5. Elastin Cat#E1146, lot#Y10590, Spectrum
6. Gluten Wheat Cat#G0066, Lot#OGH01, TCI America
7. Gluten Black Yeast Cat#G0331, Lot#6T3DJ-ML, TCI
8. Keratin [K] Cat# K3030, lot#1AG0185, Spectrum Using the above described materials and equipment, 10 mg of Keratin, Elastin, Glucan Black Yeast, Glucan Wheat and Collagen powder were each placed in a 1.5 ml centrifuge tube (5 in number). The five samples were labeled K+NPC, Collagen+SVA, Elastin+SVA, Gluten Wheat+SVA, Gluten Black Yeast+SVA. One ml of phosphate buffered saline (PBS) was added to Keratin, Glucan Black, Glucan Wheat samples and shaken for 45 minutes. One ml of phosphate buffered saline (PBS) plus 5% Acetic Acid were added to the Collagen sample and shaken for 45 minutes. One milliliter of water was added to the Elastin sample and shaken for 45 minutes. Then 100 mg of NPC was added to Keratin and placed on shaker for 30 minutes. Then 60 mg of SVA was added to Elastin, Glucan Black and Glucan Wheat and placed on shaker for 30 minutes. Then 175 mg of SVA was added to Collagen and placed on shaker for 30 minutes. The resultant solutions were stored in a freezer box with desiccant and returned to −20° C. freezer until used.

Example 7

Treatment of Human Hair with Polypeptide-polyethylene Glycol and Polysaccharide-polyethylene Glycol Compositions Human hair samples were treated with the pegylated solutions described in Examples 5 and 6. After one to five minutes, all hair samples were blown dry with a hair dryer and then treated with a flat iron with one pass over the hair. The flat iron was at setting (30) which indicated a temperature of about 446° F./230° C. and was passed over the hair at a rate of about 10 mm/second. All hair samples were rinsed with tap water for about 30 seconds.

The hair samples were then treated with hair masque/mask and allowed to set for 5 minutes. The hair samples were rinsed with tap water for 30 seconds to 1 minute until all of the hair masque material was removed and then dried using a hair dryer until fully dried. Each hair sample was analyzed for hair thickening and hair smoothing as determined by scanning electron microscopy (SEM). Hair samples were also analyzed visually without the aid of a microscope. Table 4 below provides the results of these experiments. In Table 4, T=tight, L=loose, ML=medium loose, S=smooth, R=rough, and MR=medium rough.

TABLE 4

| Sample | Results (microns) | Tight plates | Smooth surface | Observations |
|---|---|---|---|---|
| Standard hair | 50 | L | R | Light looking and dull |
| Brazilian Blowout Original Solution | 70 | L | R | Light looking and hazy |
| Keratin + MS4 | 90 | ML | MR | Smooth with color |
| Keratin + MS24 | 90 | T | S | Smooth with color |
| Keratin + TMS12 | 80 | T | S | Noticeable signs of the smoothing |
| Keratin | 70 | T | S | Light looking and hazy |
| Keratin:Polymer SVA (1:1) | 80 | T | S | Noticeable signs of the coating and smoothing |
| Keratin:Polymer SVA (1:0.3) | 90 | T | S | Smooth with color |
| Keratin:Polymer SVA (1:0.1) | 85 | T | S | Smooth with color |
| Keratin + NPC | 80 | T | S | Smooth with color |
| Collagen: Polymer SVA | 85 | L | R | Rough with bumpy coating |
| Elastin: Polymer SVA | 85 | T | MR | Tight plates but coating bumpy |
| Glucan yeast: Polymer SVA | 70 | T | S | Smooth surface but some bumps |
| Glucan wheat: Polymer SVA | 70 | T | S | Smooth surface, tight plates |
| SVA Neat | 85 | ML | MR | Smooth |
| Solution Neat | 70 | L | R | Dull |
| TMS12 Neat | 65 | ML | MR | Smooth but hazy |
| MS24 Neat | 85 | ML | MR | Smooth but hazy |
| African American hair standard | 60 | L | R | Highly curly |
| African American hair treated Keratin: MS12 (135 washes) | 60 | T | S | Tight hold on the plates, hair was still straight after treatment and had shine |
| Standard hair treated Keratin: MS12 (room temperature application) | 80 | L | R | Very loose and rough with poor qualities for hair |
| Standard hair treated Keratin: MS12 (30 washes) | 90 | T | MR | Hair remained smooth, straight and had color |
| Standard hair treated Keratin: MS12 (65 washes) | 70 | R | MR | Hair remained smooth, straight and had color |
| Standard hair treated Keratin: MS12 (100 washes) | 85 | T | MR | Hair remained smooth, straight and had color |
| Standard hair treated Keratin: MS12 (135 washes) | 80 | T | MR | Hair remained smooth, straight and had color |

Table 4 demonstrates that the polypeptide- and polysaccharide-hydrophilic polymer compositions of the present invention provide for both thickening and smoothing of the hair shaft and that these results can be obtained with varying ratios of keratin to hydrophilic polymer. Table 4 further demonstrates the surprising finding that keratin-hydrophilic polymer compositions provide for increased smoothing as compared to compositions containing only hydrophilic polymer. Similar beneficial results were found using a 30K SVA PEG reacted at a 0.1:1 ratio with Keratin using the protocol set forth in Example 5, resulting in a 90 µ SEM reading on virgin/unprocessed hair.

Example 8

Treatment of Human Hair with Various Concentrations of Keratin

Keratin compositions were prepared using the following materials and equipment:
1. Pipettes
2. Syringes
3. 1.5 ml and 10 ml centrifuge tubes
4. Weighing balance Mettler
5. DPBS-Dulbecco's phosphate buffered saline cat# 14190, lot# 1048427, Gibco
6. Keratin Cat#K3030, lot#1AG0185, Spectrum Appropriate amounts of keratin solution were added to the below indicated tubes to achieve the given keratin concentrations. All of the keratin dissolved with appearance of the solution starting at clear and gradually moving into mild yellow color in appearance.
1. Keratin=K
2. K—10 mg/ml
3. K—20 mg/ml
4. K—30 mg/ml
5. K—40 mg/ml
6. K—50 mg/ml
7. K—75 mg/ml
8. K—100 mg/ml
9. K—150 mg/ml
10. K—200 mg/ml Human hair samples were treated with the keratin solutions described above. After one to five minutes, all hair samples were blown dry with a hair dryer and then treated with a flat iron with one pass over the hair. The flat iron was at setting (30) which indicated a temperature of about 446° F./230° C. and was passed over the hair at a rate of about 10 mm/second. All hair samples were rinsed with tap water for about 30 seconds.

The hair samples were then treated with hair masque/mask and allowed to set for 5 minutes. The hair samples were rinsed with tap water for 30 seconds to 1 minute until all of the hair masque material was removed and then dried using a hair dryer until fully dried. Each hair sample was analyzed visually without the aid of a microscope.

It was observed that the 10, 20 and 30 mg/ml keratin solutions applied easily and resulted in good physical properties of hair samples. The 100 mg/ml keratin solutions also applied well to the hair but it was more difficult to move a flat iron across the hair due to stickiness. The hair properties were also good with the 100 mg/ml solution. Accordingly, keeping the keratin concentration to below 100 mg/ml may be preferred.

Example 9

Keratin-polyethylene Glycol (SVA) Compositions do not Contain Detectable Amounts of Formaldehyde by a Colorimetric Assay and less than 5 ppm Using an HPLC Assay Keratin-polyethylene glycol (SVA) compositions made as set forth in Example 5 using a 1:0.1 ratio of Keratin:PEG and a concentration of 10 mg/ml were analyzed using a formaldehyde by acetyl acetone colorimetric methodology (also known as the Japanese method). See the Journal of Food and Drug Analysis, Vol. 11, No. 1, 2003, pages 8-15. This assay detects not only formaldehyde, but also aldehyde and formaldehyde donors, and has an error range of about 10 ppm. Thus any data yielding results of less than 10 ppm will result in a "not detectable" reading. The results of the analysis were that the keratin-SVA compositions of the present invention contain less than 10 ppm formaldehyde. Since there is an estimated error rate of 10 ppm with this method, the amount of formaldehyde in the samples was considered to be not detectable.

Similar results were achieved using an industry accepted HPLC assay with pre-column derivatization with 2,4-dinitrophenylhydrazine. See Journal of Food and Drug Analysis, Vol. 11, No. 1, 2003: 8-15). The HPLC assay yielded a value of 4.31 ppm formaldehyde for the 5K SVA PEG:Keratin (0.1:1 ratio SVA PEG:Keratin) conjugates prepared as in Example 5. The inclusion of the 5K SVA PEG:Keratin (0.1:1) conjugates in a preservative system containing phenoxyethanol, caprylyl glycol, potassium sorbate, and citric acid also resulted in very low amounts of formaldehyde, 4.56 ppm. Keratin alone resulted in a 3.64 ppm result for formaldehyde by the HPLC method.

The invention claimed is:

1. A conjugate comprising
   a linear polyethylene glycol compound that is reactive on one end,
   wherein the end covalently binds to a hydrolyzed keratin polypeptide to form the conjugate; and
   wherein the conjugate is water soluble.

2. The conjugate of claim 1, wherein the linear polyethylene glycol compound has a molecular weight between about 0.5 and 80 kDa.

3. The conjugate of claim 2, wherein the molecular weight of the hydrolyzed keratin polypeptide is about 0.5 kDa to about 60 kDa.

4. The conjugate of claim 3, wherein the molecular weight of the hydrolyzed keratin polypeptide is about 2 kDa to about 6 kDa.

5. The conjugate of claim 2, wherein the molecular weight of the linear polyethylene glycol compound is between about 0.5 to about 10 kDa.

6. The conjugate of claim 4, wherein the linear polyethylene glycol compound has a molecular weight of between about 0.5 to about 10 kDa.

7. The conjugate of claim 6, wherein the molecular weight of the linear polyethylene glycol compound has a molecular weight of about 5 kDa.

8. The conjugate of claim 1, wherein the linear polyethylene glycol compound covalently binds the hydrolyzed keratin polypeptide at a primary amine or covalently binds the hydrolyzed keratin polypeptide at a sulfhydryl.

9. The conjugate of claim 1, wherein the linear polyethylene glycol compound is an N-hydroxysuccinimide functionalized PEG.

10. The conjugate of claim 5, wherein the linear polyethylene glycol compound is mPEG-Succinimidyl-Succinate, mPEG-Nitrophenyl carbonate or mPEG-Succinimidyl Glutarate.

11. The conjugate of claim 4, wherein the linear polyethylene glycol compound has between 1 and 1500 ethylene glycol repeating units.

12. The conjugate of claim 11, wherein the linear polyethylene glycol compound has between 100 and 125 ethylene glycol repeating units.

13. A composition comprising the conjugate of claim 1.

14. The composition of claim 13, wherein the composition is substantially free of formaldehyde.

15. A composition comprising the conjugate of claim 5.

16. A composition comprising the conjugate of claim 6.

17. A composition comprising the conjugate of claim 12.

18. A method of treating hair of a subject comprising contacting at least a portion of the hair with the conjugate of claim 1.

19. The method of claim 18, the method further comprising applying heat to the hair after the contacting step.

20. The method of claim 18, wherein one or more physical characteristics of the hair is improved after contacting; wherein the one or more physical characteristics are selected from the group consisting of smooth surface, smooth with color, and thickness.

21. A method of treating hair of a subject, the method comprising contacting at least a portion of the hair with the conjugate of claim 12.

22. A conjugate comprising
methoxy-poly (ethylene glycol)-succinimidyl valerate that covalently binds to a hydrolyzed keratin polypeptide to form the conjugate wherein the conjugate is water soluble.

23. The conjugate of claim 22, wherein the methoxy-poly (ethylene glycol)-succinimidyl valerate has a molecular weight between about 0.5 and 80 kDa.

24. The conjugate of claim 22, wherein the molecular weight of the hydrolyzed keratin polypeptide is about 0.5 kDa to about 60 kDa.

25. The conjugate of claim 24, wherein the molecular weight of the hydrolyzed keratin polypeptide is about 2 kDa to about 6 kDa.

26. The conjugate of claim 23, wherein the molecular weight of the methoxy-poly (ethylene glycol)-succinimidyl valerate is between about 0.5 to about 10 kDa.

27. The conjugate of claim 25, wherein the methoxy-poly (ethylene glycol)-succinimidyl valerate has a molecular weight of between about 0.5 to about 10 kDa.

28. The conjugate of claim 25, wherein the molecular weight of the methoxy-poly (ethylene glycol)-succinimidyl valerate has a molecular weight of about 5 kDa.

29. The conjugate of claim 22, wherein the linear polyethylene glycol compound covalently binds the hydrolyzed keratin polypeptide at a primary amine or covalently binds the hydrolyzed keratin polypeptide at a sulfhydryl.

30. The conjugate of claim 25, wherein the linear polyethylene glycol compound has between 1 and 1500 ethylene glycol repeating units.

31. The conjugate of claim 30, wherein the linear polyethylene glycol compound has between 100 and 125 ethylene glycol repeating units.

32. A composition comprising the conjugate of claim 22.

33. The composition of claim 32, wherein the composition is substantially free of formaldehyde.

34. A composition comprising the conjugate of claim 27.

35. A method of treating hair of a subject comprising contacting at least a portion of the hair with the conjugate of claim 22.

36. The method of claim 35, the method further comprising applying heat to the hair after the contacting step.

37. The method of claim 36, wherein one or more physical characteristics of the hair is improved after contacting; wherein the one or more physical characteristics are selected from the group consisting of smooth surface, smooth with color, and thickness.

38. A method of treating hair of a subject, the method comprising contacting at least a portion of the hair with the composition of claim 27.

* * * * *